United States Patent [19]
Odén et al.

[11] Patent Number: 5,565,152
[45] Date of Patent: *Oct. 15, 1996

[54] METHOD OF MAKING ARTIFICIAL TOOTH VENEER

[75] Inventors: Agneta E. Odén, Stocksund; Matts K. G. Andersson, Lerum, both of Sweden

[73] Assignees: Sandvik AB, Sandviken; Nobelpharma AB, Gothenburg, both of Sweden

[*] Notice: The term of this patent shall not extend beyond the expiration date of Pat. No. 5,106,303.

[21] Appl. No.: 303,001

[22] Filed: Sep. 9, 1994

Related U.S. Application Data

[63] Continuation of Ser. No. 44,714, Apr. 12, 1993, abandoned, and a continuation-in-part of Ser. No. 753,102, Aug. 30, 1991, Pat. No. 5,217,375, which is a continuation of Ser. No. 497,620, Mar. 23, 1990, Pat. No. 5,106,303, said Ser. No. 44,714, is a continuation of Ser. No. 760,925, Sep. 17, 1991, abandoned.

[30] Foreign Application Priority Data

Sep. 17, 1990 [SE] Sweden .................................. 9002959

[51] Int. Cl.⁶ .......................... A61C 13/08; C04B 33/34; C04B 41/81
[52] U.S. Cl. .................. 264/19; 264/62; 264/67; 264/162; 264/163; 427/2.27; 433/218; 433/223; 433/226
[58] Field of Search ............................ 427/2, 2.26, 2.27; 433/223, 226, 228.1, 222.1, 218; 264/16, 19, 62, 67, 129, 162, 163

[56] References Cited

U.S. PATENT DOCUMENTS

| | | |
|---|---|---|
| 3,541,688 | 11/1970 | McLean et al. . |
| 3,997,637 | 12/1976 | Rogers . |
| 4,411,626 | 10/1983 | Becker et al. . |
| 4,556,389 | 12/1985 | Ueno et al. . |
| 4,575,805 | 3/1986 | Moermann et al. . |
| 4,579,530 | 4/1986 | McLaughlin . |
| 4,585,417 | 4/1986 | Sozio et al. . |
| 4,671,770 | 6/1987 | Bell et al. . |
| 4,689,197 | 8/1987 | Groll et al. . |
| 4,772,436 | 9/1988 | Tyszblat . |
| 4,789,649 | 12/1988 | Abert et al. . |
| 4,793,809 | 12/1988 | Sigler et al. . |
| 4,842,454 | 6/1989 | Gustavsson et al. . |
| 4,937,928 | 7/1990 | van der Zel . |
| 5,024,790 | 6/1991 | Grossman et al. ............... 264/16 |
| 5,030,392 | 7/1991 | Grossman et al. ............... 264/16 |
| 5,106,303 | 4/1992 | Oden et al. . |
| 5,192,472 | 3/1993 | Andersson . |

FOREIGN PATENT DOCUMENTS

3604531A1  8/1987  Germany .

Primary Examiner—Karen Aftergut
Attorney, Agent, or Firm—Burns, Doane, Swecker & Mathis, L.L.P.

[57] ABSTRACT

A method of manufacturing artificial tooth veneer restorations for natural teeth composed of a ceramic core by pressing and sintering ceramic powder. The core is preferably manufactured from a high strength densely sintered ceramic material by copy milling from an impression of the prepared tooth surface to a compacted body, a presintered body or a sintered body. Alternatively, the core is manufactured by compacting the ceramic powder against a body, which surface is copy milled from a model of the prepared tooth surface. During the copy milling, the sintering shrinkage is considered by enlargement of that body. The tooth veneer restorations are given their final shape by shaping the external surface of the compacted, presintered or sintered ceramic body. After the final sintering, the external surface can be shaped before a veneer material is attached to the external surface of the core by firing of dental porcelain. Manufacturing ceramic teeth veneer restorations according to the method of this invention increases their strength and accuracy to shape.

10 Claims, 1 Drawing Sheet

METHOD OF MAKING ARTIFICIAL TOOTH VENEER

The present application is a continuation of application Ser. No. 08/044,714 filed Apr. 12, 1993 (now abandoned), a continuation of Ser. No. 07/760,925 filed Sep. 17, 1991 (now abandoned) and is a continuation-in-part of Ser. No. 07/753,102 filed Aug. 30, 1991 (now U.S. Pat. No. 5,217,375), a continuation of Ser. No. 07/497,620 filed Mar. 23, 1990 (now U.S. Pat. No. 5,106,303).

BACKGROUND OF THE INVENTION

In our prior U.S. patent application Ser. No. 07/497,620, we disclosed and claimed a method for making an artificial onlay tooth crown or inlay for fit into a prepared tooth cavity in which a negative reproduction of the cavity is first made, a core is copy milled from the negative reproduction including a surface abutting the cavity as well as an external surface and then a veneer was applied to at least part of the external surface of the core.

The present invention relates to methods of manufacturing accurately shaped artificial veneer restorations for natural teeth from a high strength ceramic material with powder technological methods.

Veneer restorations can be fixed on natural teeth for, e.g., aesthetic reasons, if the natural teeth are for some reason discolored. Veneer restorations can be made by using conventional dental porcelain technique on a model from the prepared tooth. The model material has no dimensional changes of importance at temperatures up to 1200° C. When the veneer restoration is ready, the model material is removed by sand blasting.

The problem with the ceramic material now used (dental porcelain) in veneer restorations is their brittleness, which often gives early fracture.

OBJECTS AND SUMMARY OF THE INVENTION

One object of the present invention is to provide artificial veneer restorations, which have high strength and accuracy to shape.

Another object is to make a veneer restoration by using densely sintered, high strength ceramic material, provided that the demand of high strength and accuracy to shape (which includes compensation for the shrinkage during sintering) can be combined with the demand on the application of porcelain concerning firing, adherence, biocompatibility and aesthetics.

In accordance with the present invention there is provided a method of making an artificial tooth veneer restoration comprising a core having an internal surface which will fit a prepared tooth surface which method comprises forming an impression of the prepared tooth surface and copy milling a body from the said impression of the prepared tooth surface, said body being either the core or a body from which the core is formed.

DETAILED DESCRIPTION OF THE PREFERRED EMBODIMENTS

Figures 1, 2:
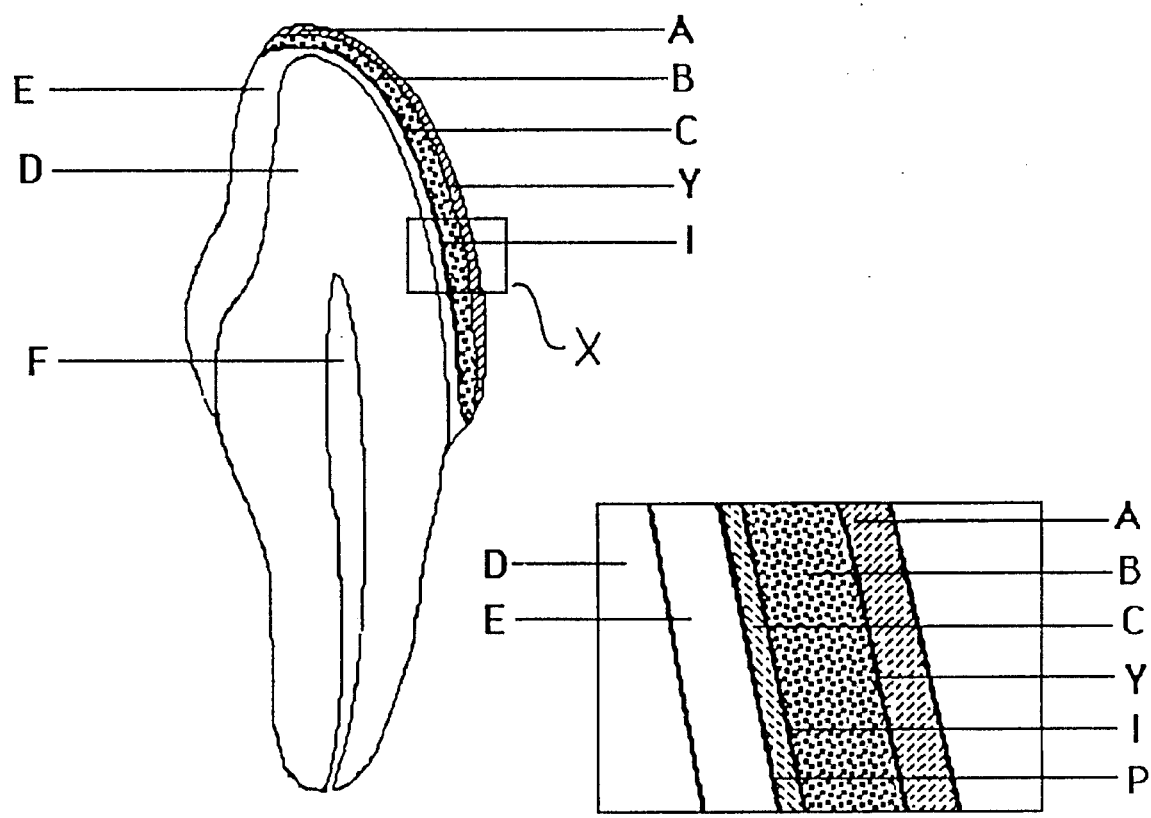
FIG. 1 shows a cross-section of a tooth with a veneer restoration. In this figure, A=porcelain fired to the core, B=core made of a densely sintered ceramic, Y=external surface of the core, I=internal surface of the core, P=the prepared surface of the tooth, C=cement, E=enamel, D=dentin and F=pulp.
FIG. 2 is an enlargement of the tooth cross-section in the box X of FIG. 1

According to the present invention, artificial veneer restorations can now be made in which the core is manufactured from a biocompatible material where the internal surface of the core has been given such shape as to fit to a prepared facial surface of a tooth. The material of the core must not give any discolorations or other unwanted effects to the dental porcelain, which usually is fired on the external surface of the core. The veneer restorations are fixed to the prepared surface by cementation. With the aid of gypsum models of the two jaws and with the manufactured core on the model of the preparation, the dental technician can make the final design of the external surface Y of the veneer restoration by grinding and polishing the core. In order to have a more natural surface of the veneer restoration, a thin layer (>50 μm) of the dental porcelain can be fired on the external surface of the core Y. The method of manufacturing a tooth veneer restoration for a prepared facial surface of a natural tooth, according to the invention, increases the strength and accuracy for this restoration.

Cores according to the invention can be made from a body of, for instance, dental porcelain, glass ceramic or apatite ceramic, by copy milling an impression from the prepared surface P. This copy milling gives the boundary surface of the veneer restoration I to the prepared surface P. An impression is made of the prepared tooth or this tooth together with its adjacent teeth. The impression material adheres to the whole prepared surface and when the impression is removed from the teeth, this impression contains the surface P, which will give the surface I and the contact points to the adjacent teeth. From the impression, the surface I is prepared in order to have this surface within reach for copy milling. The contacts with the adjacent teeth give the limitation of the veneer restoration in mesial-distal direction. The external contour outside the impression of the prepared surface P is prepared manually with conventional dental technical machining practice or by copy milling. An impression can be, e.g., a Kerr impression, with a dental composite, or a silicon impression.

Preferably, the core according to the invention, is made from a biocompatible, densely sintered, high strength ceramic material. Porcelain is fired on the core obtained so that the final product will be a tooth veneer restoration which will fit to an existing tooth preparation and aesthetically and functionally to the actual whole set of teeth.

As can be seen from FIGS. 1 and 2, artificial veneer restorations are made as a core in densely sintered ceramic B with a fired thin layer of dental porcelain A. The veneer restoration is fixed to the prepared surface P by, e.g., cementing. The thin layer of cement C connects the prepared tooth surface P with the internal surface of the core I which fits with high accuracy against the prepared surface P. The layer of cement can have a thickness<100 μm, preferably 25–50 μm. The cementing of the veneer restorations can be made with, e.g., some resin-based cement. It can be an advantage to silane treat the surfaces I of the veneer restoration which will be joined with the prepared surfaces of the tooth structure P. It can also be an advantage to etch the enamel parts E of the prepared surface P. Etching medium can be, e.g., phosphoric acid. Dentin parts of the prepared surface can, before cementing, be treated with some dentin adhesive.

The ceramic powder can be made by several methods well-known to the skilled artisan. Conventional powder technology can be used where the different components are mixed and milled under dry or wet conditions with water or an inorganic solvent, e.g., alcohols, as milling liquid. The so-called SOL-GEL technique can also be used where different oxide materials are deposited together from a water solution or are co-precipitated from metal alcoxides in, e.g., water free alcohol, by controlled addition of water. A combination of different techniques can also be used by using SOL-GEL technique to deposit a surface layer of desired metal oxide on a powder material. To the ceramic slurry, lubricants or other organic binders are added when needed at a suitable time in the process.

According to the invention, artificial tooth veneer restorations can now be manufactured from a ready to press powder with additions of lubricants and/or other organic binders. The powder is cold isostatically compacted, uniaxially pressed, slip cast, pressure cast, injection molded or compacted in another way. The compacted body has such a dimension that it contains enough material for the copy milling of the outer shape of the core, which will fit to the prepared tooth surface. During this copy milling, the sintering shrinkage must be considered. Thus, the copy milled surface must be enlarged so that after the subsequent sintering process to high density, the core has, with great accuracy, the desired final geometrical external shape which will fit to the prepared tooth surface P. The body can also be presintered before the copy milling of the surface I, fitting to the prepared surface P. All the other surfaces are prepared near final shape before the final sintering, which means a thickness of the veneer restoration of<1 mm. In some places where the prepared tooth has larger damage, the veneer restoration can be thicker. It is important that the ceramic material is sintered to closed porosity, which for an oxide material means at least 98% of theoretical density, but in order to ensure high mechanical strength, the material should preferably have a density over 99%, while densities over 99.5% give the best strength. In some cases, it can be suitable to use a finally sintered body, in which case the sintering shrinkage need not to be considered during the copy milling.

The core of the veneer restorations can also be made by cold isostatic pressing, uniaxial pressing, slip casting, pressure casting, injection molding or compacting in another way against a body uniform with the prepared surface of the tooth P to which the veneer restoration will fit. This body is made by copy milling and at the same time enlargement from a model in gypsum of the prepared tooth. The body can be made from, e.g., metallic material, graphite, plastic material, and shall have such a size that the internal surface I of the veneer restoration after the sintering shrinkage has the desired fit against the prepared tooth surface P. The copy milled surface of the body will give the internal shape of the core I. The external shape of the core Y is made by grinding and milling mostly before the sintering. After the sintering, the external surface Y of the core B is adjusted by grinding so the veneer restoration fits to the prepared tooth and to the teeth in the two jaws.

The sintering takes place in vacuum or under hydrogen atmosphere, under normal atmospheric pressure or under increased pressure in connection with hot isostatic compaction. Highly pure $Al_2O_3$ becomes translucent during sintering to full density in vacuum or in hydrogen atmosphere, which is an advantage when natural teeth are to be imitated. Pure oxide material can be sintered in air, but some composites should be sintered in inert or controlled atmosphere.

The core is given an external shape so that the building-up of the dental porcelain is facilitated. The shape can also be such that it is roughly similar to natural teeth. After the final sintering, the surfaces of the core may need some grinding, especially the external surfaces, which is made with the veneer restoration on a model of the prepared tooth. If dental porcelain is used, the thermal expansion must be adapted to the material in the core. In the case of $Al_2O_3$, there will even be a "chemical" bond between $Al_2O_3$ and porcelain. This means that the external surface of the core does not need any retention elements. The core can also be given such a shape and color that the veneer restoration does not need any dental porcelain layer. The surfaces of the veneer restoration which are a part of the external surface of the repaired tooth must, in this case before the cementing, be ground and polished to a surface roughness of 0.5–5 µm, preferably 0.5–1 µm.

The ceramic base material in the core preferably comprises one or more biocompatible oxides (including phosphates, silicates and sulphates), with additives of carbides, silicides, nitrides or borides with or without binder metal. The base material can also comprise nitrides, oxynitrides, sulphides, oxysulphides or similar phases as well as ceramic substances containing halogens. Examples of biocompatible oxides, which can form base matrix for the ceramic body, are $Al_2O_3$, $TiO_2$, MgO, $ZrO_2$, and $ZrO_2$ with additives of up to 25 mole%, preferably 10 mole% of $Y_2O_3$, MgO and/or CaO (partly or totally stabilized $ZrO_2$). In a preferred embodiment, the ceramic material comprises>50%, preferably >85% of $Al_2O_3$ with additives of conventional sintering aids. In order to increase the strength, <25% weight, preferably 3–12% weight of $ZrO_2$ can be added.

In order to get a suitable color of the core B, colored components can be chosen. Additives, e.g., 0.1–10% weight, preferably 0.5–5% weight of TiN and/or ZrN will give $Al_2O_3$ based teeth veneer restorations a faint yellow shade. Of course, no additives used will give unaesthetic effects.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A method of manufacturing a veneer restoration for a facial surface of a tooth to be restored, comprising steps of:

preparing an impression of a facial surface of a tooth to be restored;

copy milling a copy milled surface on a core by using the impression to provide the copy milled surface on the core, the copy milled surface having a shape larger than and corresponding to the facial surface of the tooth, the larger shape allowing for shrinkage of the core during sintering of the core; and shaping an external surface of the core into a final shape corresponding to a facial surface of the veneer restoration.

2. The method of claim 1 wherein the core comprises a high-strength ceramic material with a density>98%.

3. The method of claim 2 wherein the core comprises a high-strength ceramic material with a density>99%.

4. The method of claim 2 wherein the ceramic material of the core is an oxide selected from the group consisting of $Al_2O_3$, $TiO_2$, MgO, $ZrO_2$ and mixtures thereof, or $ZrO_2$ with up to 25 mole% of an oxide selected from the group consisting of $Y_2O_3$, MgO, CaO and mixtures thereof.

5. The method of claim 2 wherein the ceramic material comprises $Al_2O_3$.

6. The method of claim 1 wherein the copy milling step is carried out such that the copy milled surface is sized to allow for shrinkage of the core during sintering, the method further comprising sintering the core subsequent to the copy milling step, the core undergoing shrinkage during the sintering step.

7. The method of claim 1 further comprising applying and firing dental porcelain to the external surface of the core.

8. The method of claim 1 further comprising sintering the core prior to the copy milling step.

9. The method of claim 1 further comprising sintering the core subsequent to the shaping and copy milling steps, the core undergoing shrinkage during the sintering step.

10. The method of claim 1 further comprising sintering the core and then grinding the final shape of the external surface of the core to fit teeth adjacent the tooth having the facial surface to be restored.

* * * * *